US012144947B2

(12) United States Patent
Alleyne, Jr. et al.

(10) Patent No.: US 12,144,947 B2
(45) Date of Patent: Nov. 19, 2024

(54) METHOD OF REMOVING FLUID FROM THE BODY, AND DEVICE THEREFORE

(71) Applicants: AUGUSTA UNIVERSITY RESEARCH INSTITUTE, INC., Augusta, GA (US); Kayyani C. Adiga, Macon, GA (US)

(72) Inventors: Cargill H. Alleyne, Jr., Martinez, GA (US); Kayyani C. Adiga, Macon, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 246 days.

(21) Appl. No.: 17/944,571

(22) Filed: Sep. 14, 2022

(65) Prior Publication Data

US 2023/0001166 A1   Jan. 5, 2023

Related U.S. Application Data

(63) Continuation of application No. 16/394,570, filed on Apr. 25, 2019, now Pat. No. 11,458,288.
(Continued)

(51) Int. Cl.
*A61M 27/00* (2006.01)
*A61M 11/00* (2006.01)

(52) U.S. Cl.
CPC ........ *A61M 27/006* (2013.01); *A61M 11/005* (2013.01); *A61M 2210/0687* (2013.01); *A61M 2210/0693* (2013.01)

(58) Field of Classification Search
CPC .............. A61M 27/006; A61M 11/005; A61M 2210/0687; A61M 2210/0693
See application file for complete search history.

(56) References Cited

U.S. PATENT DOCUMENTS 6,273,342 B1   8/2001   Terada et al.
9,533,323 B2   1/2017   Sauzade
(Continued)

FOREIGN PATENT DOCUMENTS

CA   2 504 249 C   8/2013
CN   101557882 A   10/2009
(Continued)

OTHER PUBLICATIONS

International Search Report for International Patent Application No. PCT/US2019/029124, dated Dec. 19, 2019 (2 pages in English).
(Continued)

*Primary Examiner* — Rebecca E Eisenberg
*Assistant Examiner* — Kate Elizabeth Strachan
(74) *Attorney, Agent, or Firm* — Smith, Gambrell & Russell, LLP

(57) ABSTRACT

A method for removing bodily fluid includes drawing bodily fluid that has accumulated in excess, converting the drawn fluid from bulk liquid form to aerosol form, and disposing of the aerosol via evaporation of liquid droplets and absorption and/or diffusion of vapor. Conversion from bulk liquid to aerosol may include collecting the bulk liquid fluid in a reservoir, conveying the bulk liquid bodily fluid to an atomizer, converting the bulk liquid fluid into an aerosol having ultrafine droplets, and ejecting the aerosol into a subcutaneous space for disposal via evaporation of liquid droplets and absorption and/or diffusion of vapors. The method may be performed with a subcutaneous atomizer that may be controlled locally or by an external transmitter for effecting a conversion and mist rate to keep pace with the accumulation of excess bodily fluid.

33 Claims, 7 Drawing Sheets

Related U.S. Application Data

(60) Provisional application No. 62/662,927, filed on Apr. 26, 2018.

(56) References Cited

U.S. PATENT DOCUMENTS

| | | |
|---|---|---|
| 2005/0159697 A1 | 7/2005 | Dextradeur et al. |
| 2009/0112308 A1 | 4/2009 | Kassem |
| 2011/0282268 A1* | 11/2011 | Baker .................. A61M 31/00 604/20 |

FOREIGN PATENT DOCUMENTS

| | | | |
|---|---|---|---|
| CN | 103842019 A * | 6/2014 | .......... A61M 27/006 |
| EP | 0 718 046 A2 | 6/1996 | |
| JP | 2003-520079 A | 7/2003 | |
| WO | 2019/240885 A2 | 12/2019 | |

OTHER PUBLICATIONS

Alleyne, C.H., et al., "The Efficacy and Cost of Prophylactic and Periprocedural Antibiotics in Patients with External Ventricular Drains" Neurosurgery, vol. 47, No. 5, 1124-1127, (2000).

Kesser, C.K., et al., "New Aerosol Delivery Devices for Cystic Fibrosis" Respiratory Care, vol. 54, No. 6, 754-768, (2009).

Reddy, G.K., et al., "Ventriculoperitoneal Shunt Surgery and the Incidence of Shunt Revision in Adult Patients with hemorrhage-Related Hydrocephalus" Clinical Neurology and Neurosurgery, 114, 1211-1216 (2012).

Uchechi, O., et al., "Nanoparticles for Dermal and Transdermal Drug Delivery" Application of Nanotechnology in Drug Delivery, (2014) DOI: 10.5772/58672.

International Preliminary Report on Patentability dated Oct. 27, 2020 for International Patent Application No. PCT/US2019/029124 (6 pages).

Written Opinion dated Dec. 19, 2019 for International Patent Application No. PCT/US2019/029124 (5 pages).

* cited by examiner

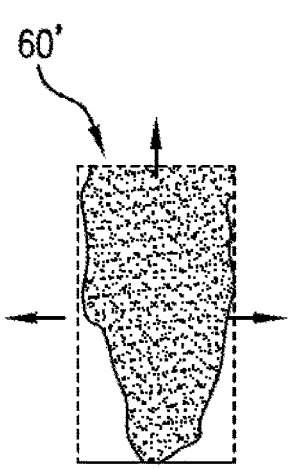 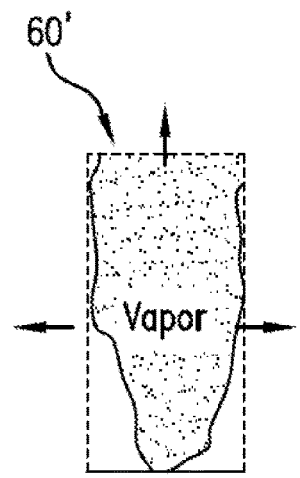
FIG.8A　　　　　　　　FIG.8B
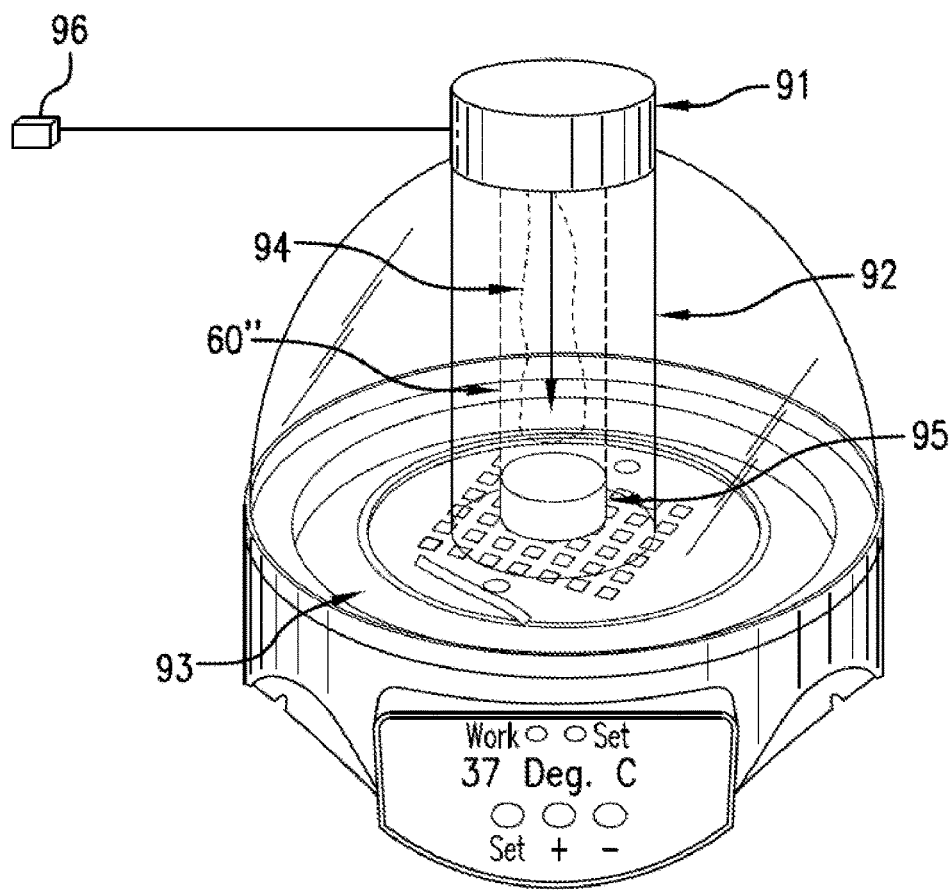
FIG.9

METHOD OF REMOVING FLUID FROM THE BODY, AND DEVICE THEREFORE

FIELD OF THE INVENTION

The present invention relates to a method of removing fluid from the body, including Cerebrospinal fluid in the treatment of hydrocephalus, and a device therefore.

BACKGROUND OF THE INVENTION

There are a number of ailments that are characterized by the accumulation of excess fluid within a subject's body, and for which at least one recommended treatment is the removal of some or all of the excess fluid. One example of such an ailment is Hydrocephalus, which results from excess Cerebrospinal fluid.

Cerebrospinal fluid (CSF) is a clear, colorless body fluid produced primarily in the choroid plexus of the ventricles of the brain. This fluid acts as a cushion or buffer for the brain, providing basic mechanical and immunological protection to the brain inside the skull. CSF is constantly being produced and reabsorbed within the body, with absorption occurring primarily in the arachnoid granulations.

Hydrocephalus ("increased water on the brain") is a condition characterized by an imbalance between a relatively greater production rate of CSF and a relatively lesser absorption rate of said CSF such that there is an excess of CSF. The condition typically results in increased intracranial pressure which may be accompanied by a wide variety of secondary symptoms, including headaches, vomiting, nausea, papilledema, sleepiness, seizures and coma. Highly elevated intracranial pressure may even result in uncal or tonsillar herniation, and brain stem compression.

Traditional treatments for hydrocephalus included drainage of excess CSF, with early treatments having been first described in the tenth century. More modern treatments include CSF diversion. Specifically, between 1898 and 1925, there were developed a variety of shunts for diverting CSF from the lumbar cistern to the peritoneum, and from the ventricle to the peritoneum, venous system, pleural cavity, and ureter. Early CSF diversion shunts had a high failure rate, due mainly to inadequate implant materials. Treatment success rates have since improved with the development of silastic tubing and artificial valves, as well as adjustable, self-regulating valves and antisiphon devices. Currently, CSF diversion remains the common treatment method with shunting of CSF from the ventricle to a variety of body cavities, most commonly the peritoneal cavity.

However, CSF diversion via current shunting methods remains suboptimal. The most common type of shunting (ventriculoperitoneal, or VP shunting) typically includes tunneling a considerable length of tubing under the skin and into the peritoneum. FIG. 1 shows one example of VP shunting, wherein a ventricular catheter is inserted into the ventricles and connected with a shunt valve that is in turn connected to a peritoneal catheter that is tunneled behind the ear and through the subcutaneous tissue of the neck and thorax and into the peritoneal cavity. This approach to CSF shunting presents risks of infection, occlusion, disconnection, migration, discomfort, pseudocyst formation, bowel injury and other issues. Furthermore, there remains a relatively high failure rate of such shunts, with an over 50% rate of shunt revision being observed in some series. See Reddy G K: Ventriculoperitoneal shunt surgery and the incidence of shunt revision in adult patients with hemorrhage-related hydrocephalus, Clinical Neurology and Neurosurgery 114, 1211-1216, 2012; and Alleyne C H, Hassan M, Zabramski J M: The efficacy and cost of prophylactic and periprocedural antibiotics in patients with external ventricular drains, Neurosurgery 47:1124-1129, 2000.

Accordingly, there remains a need in the art for a method and device for removing excess CSF that presents reduced risks to the patient, as well as reduced risks of failure and shunt revision. Preferably, an improved method and device for removing CSF will also be applicable for safely removing other fluids from a patient, including other fluids that may accumulate in the brain or fluids that may accumulate in other portions of the body.

SUMMARY OF THE INVENTION

The present invention is inclusive of a method of removing excess fluid from the body and a device therefore. The method and device are applicable for use in removing excess CSF in the treatment of hydrocephalus, and the following disclosure describes the invention in the context of such a treatment, though the invention is not limited to that specific treatment and may be used in the treatment of a number of other ailments.

A method according to the present invention includes treating hydrocephalus by drawing excess CSF from the ventricles of a patient's brain in a bulk liquid form, and directing that excess CSF toward a subcutaneous space, where the excess CSF may be converted from the bulk liquid form into another form that is readily evaporated or diffused through the subject's skin. More specifically, a ventricular catheter inserted in the ventricles of the subject's brain may withdraw excess CSF and deliver it to an atomizer implanted in a subcutaneous space between the subject's skull and scalp. The atomizer disposes of CSF through fine atomization and vapor transport processes. More specifically, the atomizer converts CSF fed thereto a bulk liquid form to a low-velocity aerosol of ultrafine CSF droplets measuring below 10 microns in diameter. Due to their extremely small size, and reduced pressure in the subcutaneous cavity, the ultrafine CSF droplets evaporate at a body temperature of 37° C. Remaining CSF vapors are disposed by absorption into a capillary bed and bloodstream of the subject and/or by diffusion through subject's scalp and skin as perspiration.

A device according to the present invention is in the form of a subcutaneous atomizer having a housing with an inlet that opens toward a reservoir for receiving CSF in a bulk liquid form and an outlet for outputting a CSF aerosol. An aerosol generator is provided in the housing for outputting a CSF aerosol and fluid conveyor is joined to the aerosol generator and extends into the reservoir for transferring bulk liquid CSF from the reservoir to the aerosol generator. The device is adapted for connection with a ventricular catheter in a manner to provide fluid communication with the housing inlet for feeding bulk liquid CSF to the housing reservoir. A power source and controller are provided for driving the fluid conveyor and/or aerosol generator to transfer bulk liquid CSF from the reservoir to the aerosol generator and to convert CSF from a bulk liquid into a low-velocity aerosol of ultrafine CSF droplets.

In one example, the aerosol generator is a piezoelectric transducer having a perforated mesh, the perforated mesh being positioned at the outlet of the housing and dimensioned such that the CSF aerosol output therethrough comprises droplets having diameters measuring between about 0.5 to 10 microns, preferably between about 0.5 to 5 microns, and more preferably between about 0.5 to 2.5 microns. The fluid conveyor may be any structure or medium suitable for transferring bulk liquid CSF, examples of which may include a spring-loaded porous wick and a silica gel structure. The controller may include a power source, as well as a variable energy module adapted to vary power output to the aerosol generator between two or more power settings, which may include a zero-power setting for powering off the device.

In another example, the aerosol generator is a piezoelectric transducer that is inclusive of a metal plate in which low frequency surface vibrations can be induced. Construction of such a piezo-plate example may include positioning a metal plate at the center of a piezoelectric transducer similar to the mesh example; or by using a piezoelectric metal plate in place of the combined transducer and mesh in the mesh example. In this example, the metal plate may be made to vibrate sufficiently to generate an aerosol comprising droplets having diameters measuring between about 0.5 to 10 microns, preferably between about 0.5 to 5 microns, and more preferably between about 0.5 to 2.5 microns. As with the mesh example, the fluid conveyor may also be any structure or medium suitable for transferring bulk liquid CSF, including a spring-loaded porous wick or a silica gel structure; though in this example the fluid conveyor will be constructed to deliver bulk liquid CSF to a top surface of the metal plate, rather than through a mesh structure. As with the mesh example, the controller may include a power source, as well as a variable energy module adapted to vary power output to the aerosol generator between two or more power settings, which may include a zero-power setting for powering off the device.

Both the foregoing general description and the following detailed description are exemplary and explanatory only and are intended to provide further explanation of the invention as claimed. The accompanying drawings are included to provide a further understanding of the invention; are incorporated in and constitute part of this specification; illustrate embodiments of the invention; and, together with the description, serve to explain the principles of the invention.

BRIEF DESCRIPTION OF THE DRAWINGS

Further features and advantages of the invention can be ascertained from the following detailed description that is provided in connection with the drawings described below:

FIGS. 8A and 8B are schematics representations of comparative results from testing the first prototype, FIG. 8A representing a greater absorption of aerosolized fluid, and FIG. 8B representing a greater evaporation and diffusion of aerosolized fluid;

FIG. 9 is a schematic representation of a second prototype of an atomizer of FIG. 2;

DETAILED DESCRIPTION OF THE INVENTION

The following disclosure discusses the present invention with reference to the examples shown in the accompanying drawings, though does not limit the invention to those examples.

The present invention is inclusive of a novel method for treating hydrocephalus that is expected to obviate the need for tunneling a catheter through the subcutaneous tissues of a subject's neck, thorax and peritoneal cavity, and a device for effecting such treatment method.

The method includes drawing excess CSF from the ventricles of a patient's brain in a bulk liquid form, converting the CSF from the bulk liquid form into a low-velocity CSF aerosol of ultrafine CSF droplets, and disposing of the CSF aerosol through biological processes. Specifically, due to their extremely small size, and reduced pressure in the subcutaneous cavity, the ultrafine CSF droplets are evaporated at a body temperature of 37° C. The remaining CSF vapors are absorbed into a capillary bed and bloodstream of the subject and/or by diffused through the subject's scalp and skin as perspiration.

The device includes a subcutaneous biological atomizer that effects CSF disposal through fine atomization and vapor transport processes. More specifically, the atomizer converts CSF fed thereto from a bulk liquid form into a low-velocity aerosol of ultrafine CSF droplets measuring below 10 microns in diameter. The atomizer includes a housing having an inlet for the introduction of CSF in a bulk liquid form and an outlet for the ejection of CSF in an aerosol form. The housing inlet is in fluid communication with a reservoir that supplies fluid to a fluid conveyor extending from the reservoir to an aerosol generator. A controller and power source are provided for effecting transfer of CSF along the fluid conveyor, from the reservoir to the aerosol generator, and driving the aerosol generator to convert CSF from a bulk liquid into an aerosol of ultrafine CSF droplets. The atomizer may be realized in a number of different constructions.

When implanted in a subject, as a cranial implant, the subcutaneous atomizer will be positioned against the skull and below the scalp of a subject, and joined with a fluid feed transport that is adapted for transporting CSF from the subject and into the atomizer. The CSF feed transport may be provided in the form of a ventricular catheter, with a first end inserted into the ventricles of the subject and a second end joined in fluid communication with the inlet of the atomizer housing.

Figure 1:
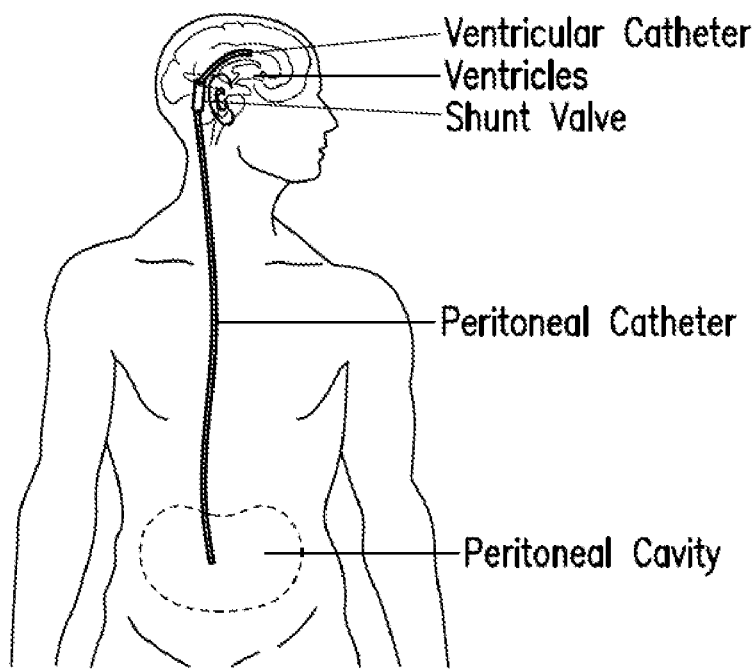
FIG. 1 shows a conventional ventriculoperitoneal shunting assembly.
Figure 2:
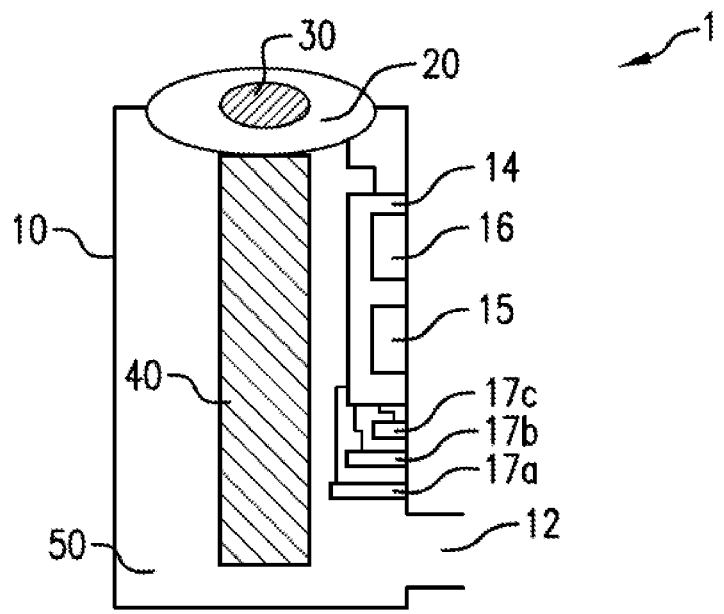
FIG. 2 shows an example of an atomizer according to the present invention.

FIG. 2 shows one example of an atomizer 1 that is inclusive of a housing 10 having an inlet 12 at one end and an outlet (covered by a perforated mesh 30) at another end. A controller 14 is provided with a power source 15 and circuitry for generating and outputting electrical signals. In this example, an aerosol generator is provided in the form of a piezoelectric mesh transducer that includes a piezoelectric transducer 20 and a perforated mesh 30 that is adapted to vibrate in response to electrical signals received from the controller 14. The perforated mesh 30 is positioned at the center of the transducer 20 to align with the housing outlet.

Though not shown in the figures, the housing may include an upper surface that covers the piezoelectric mesh transducer, and which contains a large number of holes therein for dispersal of the CSF aerosol ejected through the mesh 30. The holes in the upper surface may be dispersed over an upper region of the upper surface so as to align with the perforations of the mesh 30 and enable a direct flow of ejected CSF aerosol from the mesh 30 through the holes in the upper surface and/or the holes in the upper surface may be dispersed around a periphery of the upper surface so as to be oriented at an angle relative to the perforations of the mesh 30 and thereby require a redirection of the ejected CSF aerosol so as to promote distribution of the CSF aerosol to a greater region outside the atomizer 1.

Preferably, a spring-loaded porous wick 40 is provided as a fluid conveyor that is joined with and extends downward from the mesh 30 and into a reservoir 50. The wick 40 is dimensioned and positioned to extend into the reservoir 50 to such a length that a bottom end 42 thereof is substantially near to a bottom surface of the reservoir 50. This arrangement of the wick 40 promotes submersion of the bottom end 42 below the surface of even a minimal volume of CSF in the reservoir 50, thereby enabling processing of even minimal volumes of CSF. In this example the inlet 12 is provided adjacent to the reservoir 50 so as to enable immediate introduction of CSF feed directly to the reservoir 50.

In another example, the aerosol generator may instead be constructed with a metal plate in which low frequency surface vibrations may be induced. Such a construction may be similar to that of the mesh construction, though replacing the mesh 30 at the center of the piezoelectric transducer 20 with a solid plate. Alternatively, both the transducer 20 and the mesh 30 may be replaced by a piezoelectric metal plate. Vibration of the metal plate produces waves on the free surface of the plate, with droplets breaking off from the wave crests when wave amplitude is above a critical value.

The metal plate example would require a variation to the fluid conveyor (e.g., the porous wick, silica gel, etc.) to deliver bulk liquid to a top surface of the metal plate—e.g., by wrapping the wick 40 around an edge of the metal plate. In one construction of the metal plate example, the reservoir 50 may be constructed as a circular reservoir extending around a perimeter of the atomizer 1, with the aerosol generator positioned at a center of the atomizer 1 and separated from the reservoir 50 by a vertically oriented dividing wall. The dividing wall may include an opening through which the fluid conveyor extends, with the fluid conveyor adapted to transport bulk liquid CSF from the reservoir 50 to the metal plate of the aerosol generator.

Preference may be given to either the mesh or metal plate constructions. Regardless of the construction chosen, the aerosol generator is adapted to generate an aerosol comprising droplets having diameters measuring between about 0.5 to 10 microns, preferably between about 0.5 to 5 microns, and more preferably between about 0.5 to 2.5 microns—be it by atomizing through a mesh structure, off a vibrating surface, or otherwise. However, as the desired size of droplets decreases, preference might be given to use of the metal plate example over the mesh example, as an increased possibility of pore clogging may be observed with reduced pore sizes that would be required for achieving smaller droplet sizes (e.g., 5 microns or less). Also, it is expected that atomization via surface vibrations with a metal plate example would require less energy than atomization by forcing fluid through pores in a mesh example, and that the surface vibrations of a metal plate example will likely produce relatively shorter plumes of lower momentum as compared to a mesh example.

The power source 15 may be provided in a number of different forms, including a power-storage source or a power-relay source. For example, the power source 15 may be a removable and replaceable battery-type power source. In such an example, the power source 15 will preferably be positioned behind a releasable panel in a surface of the housing 10. This will permit the atomizer 1 to be implanted in a subject with the releasable panel oriented outwardly from the subject's skull so as to reside just below the scalp of the subject. In this way, if needed, the power source 15 may be removed and replaced with a new power source via a simple incision in the subject's scalp to expose the releasable panel, thereby enabling opening of the panel and removal and replacement of the power source 15, followed by replacement of the releasable panel and stitching of the subject's scalp. In some examples, such a releasable panel may extend along an entire surface of the atomizer housing 10, so as to permit access to all components within the housing 10, thereby enabling repair and/or replacement of any component therein.

Figure 5:
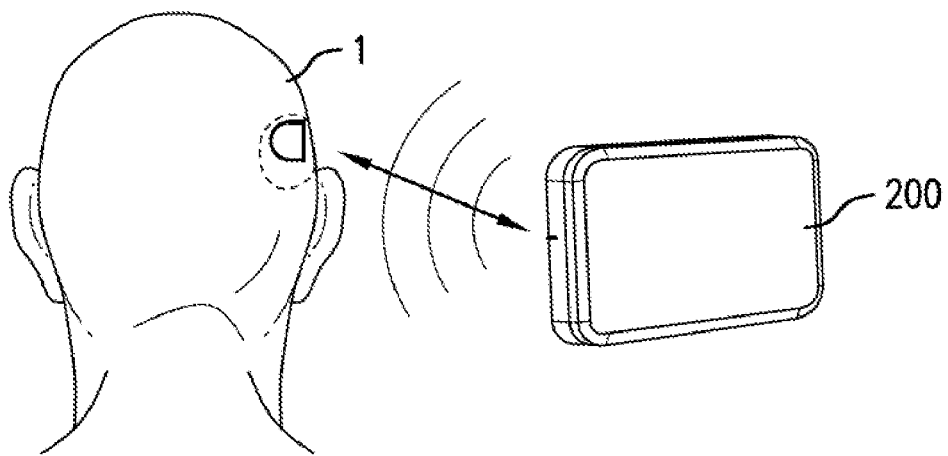
FIG. 5 shows an implanted atomizer of FIG. 2 communicating with a first external device.

In another example, the power source 15 may be a rechargeable power source adapted to convert energy from a source external to the atomizer 1, and external to the implant, into an energy for storage and use within the atomizer 1. For example, as shown in FIG. 5, the power source 15 may be an inductive power source adapted to convert electromagnetic signals received from an external device 200, outside the subject, into electrical energy for storage within the atomizer 1. In such examples, the rechargeable power source 15 and external device 200 will be synced for dedicated communication without interference by other unrelated devices and signals, and charging of the power source 15 will require that the external device 200 be brought into close proximity of the power source 15. The external device 200 may be a wearable device, and may be affixed to a clothing item such as a headband or hat for positioning near to the implanted atomizer 1. The external device 200 may instead be affixed to a non-wearable item that is regularly positioned near to the implanted atomizer 1, such as a pillow or headrest of a seat.

Figure 6A:
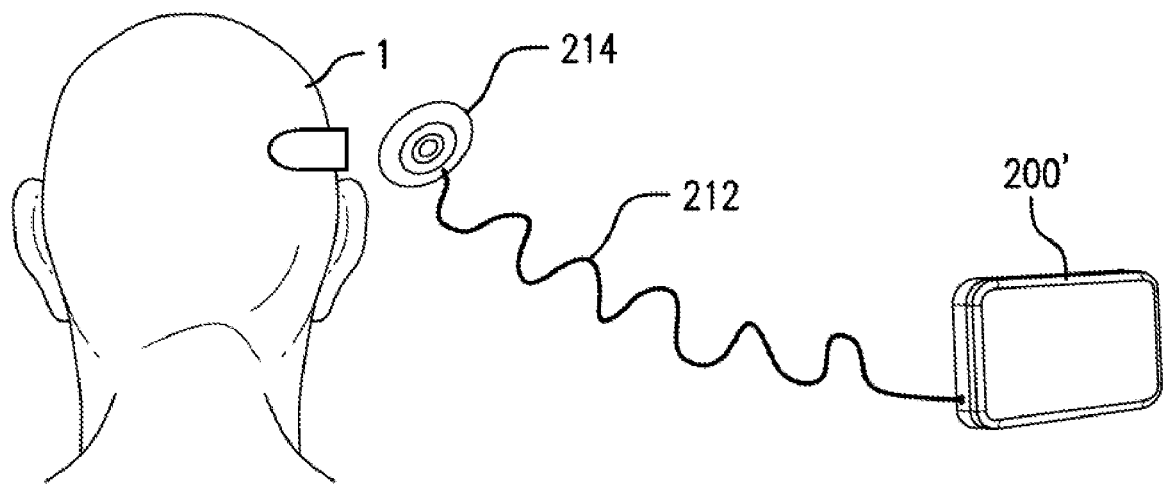
FIG. 6A shows an implanted atomizer of FIG. 2 communicating with a second external device.
Figure 6B:
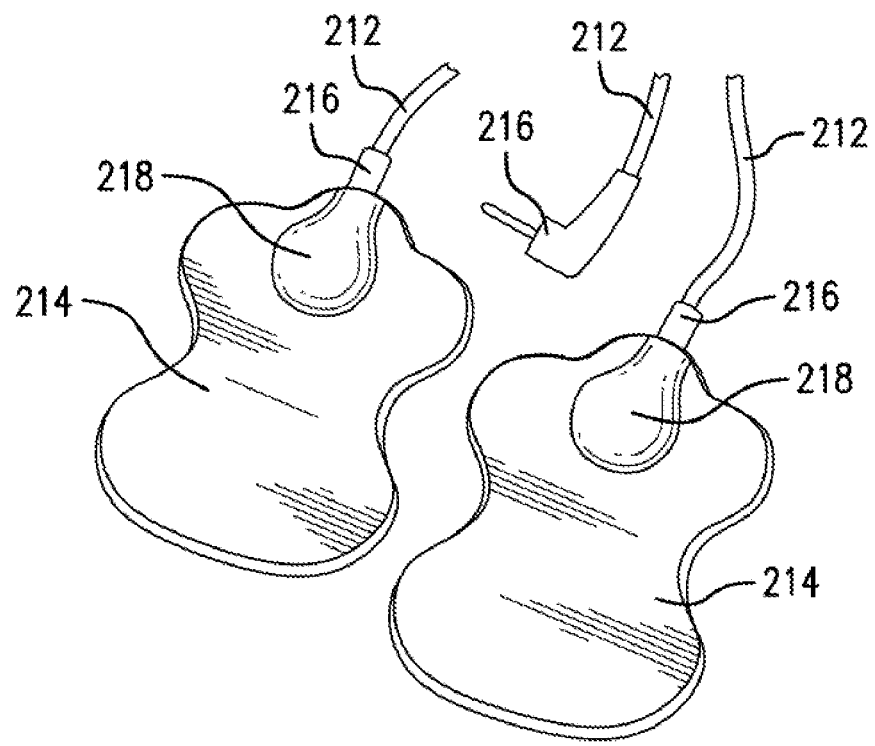
FIG. 6B shows transmitters of the second external device of FIG. 6A.

In another variation, as shown in FIG. 6A, the power source 15 may be adapted to convert electromagnetic signals received from an external device 200' that is provided in the form of a drive unit 210 that outputs electromagnetic signals through a transmitter 214 that is adapted for placement on the patient's skin, proximate to the implanted atomizer 1. The transmitter 214 may be provided in the form of an electrode having an inner induction coil and an outer adhesive layer that enables repeated adherence and removal of the transmitter 214 directly to the patient's skin, proximate to the implanted atomizer 1. The adhesive layer may include a gel, solution, and/or paste having conductive properties that promotes transmission of electromagnetic signals, such as those known to be used with Electroencephalography (EEG) probes. This variation of the external device may be desirable in instances where the subject wishes to use an external device without having to maintain the entire external device beside their head and/or without requiring use of an accessory piece of apparel to conceal the external device. By providing the external device 200' with a drive unit 210 in the form of a remote body that is separate from the transmitter 214, the subject may wear the transmitter 214 without having to place the power source of the drive unit 210 beside their head. Also, if the implanted atomizer 1 is positioned behind the subject's ear, a subject wearing the external device 200' may, on casual inspection, appear merely as though they are wearing a common earphone joined to a telecommunications or other entertainment device, thereby providing the subject with an increased comfort in their outward appearance if choosing to use the external device in a public setting. As shown in FIG. 6B, the transmitter 214 may be adapted for releasable connection with the transmission wire 212, for example by male/female connectors 216/218, so as to readily permit replacement of the transmitter 214 in the event the inner induction coil and/or outer adhesive layer break or otherwise become unusable. The drive unit 210 may also be adapted for releasable connection with the transmission wire 212, for example by male/female connectors, so as to readily permit replacement of the transmission wire 212.

In another example, the rechargeable power source 15 may be a kinetically rechargeable power source adapted to convert kinetic energy from the subject's movements (e.g., walking, head movements, etc.) into electrical energy. As another example, the rechargeable power source 15 may be a solar-cell rechargeable power source adapted to convert light energy (e.g., natural or artificial light rays) into electrical energy. In examples employing a solar-cell rechargeable power source, an outer surface of the atomizer housing 10 may be made to incorporate photovoltaic cells, and the atomizer 1 may be implanted such that the photovoltaic cells protrude through the scalp or reside at a minimal subcutaneous depth below the scalp, so as to promote the capture of light energy that penetrates an outer layer of the scalp.

In yet further examples, the power source 15 may be provided as a power relay source adapted to receive and relay energy from an external power source, without requiring any internal storage of energy within the atomizer 1. For example, a power relay source may be provided in the form of a transducer adapted to convert energy from a source external to the atomizer 1 into an energy for immediate transmittal to components of the atomizer 1. Such a power relay source may be provided with similar constructions as previously discussed relative to rechargeable type power sources, with the relay of power from the power source 15 requiring an external device 200/200' be brought into close proximity of the power source 15, though without the power source acting to storing energy within the atomizer 1. For example, the power source 15 may be an inductive energy transducer (e.g., a Hall sensor) adapted to convert an electromagnetic signal received from an external device 200/200', such as those shown in FIGS. 5 and 6A, into electrical energy that is immediately output for driving one or more components of the atomizer 1. In some examples, a power-relay source may be incorporated directly into one or more components of the atomizer 1, without need for a separate, independent power source. For example, in a construction such as that shown in FIG. 2, the piezoelectric transducer 20 of the aerosol generator could be adapted as a piezoelectric crystal having a specific resonance frequency such that the transducer 20 may directly receive and convert energy signals from an external device 200/200' that is adapted to output an electromagnetic signal at the specific resonance frequency. In such an example, the atomizer 1 may be constructed without need of a separate power source 15, which may either be omitted from the device or provided as a back-up redundancy. It is also contemplated that a power relay source may be provided in the form of a kinetic energy transducer or a solar-energy transducer, similar to the discussions above relative to rechargeable type power sources, though without the need for storing energy within the atomizer 1.

The controller 14 provides signals to control the various components of the atomizer 1, which may include outputting signals to control the fluid conveyor to effect transfer of CSF from the reservoir 50 to the aerosol generator and/or outputting signals to control the aerosol generator to effect conversion of CSF from a bulk liquid to an aerosol of ultrafine CSF droplets. One benefit of an atomizer 1 such as that shown in the example of FIG. 2 is that the controller 14 need only transmit signals to the aerosol generator, which is provided in the form of a piezoelectric mesh transducer. Specifically, the controller 14 may output signals to effect vibration of the piezoelectric transducer 20, which in turn will cause a pumping action in the spring-loaded wick 40 that is joined to the mesh 30 at the center of the transducer 20, the pumping action being effective to convey CSF up the wick 40 and toward the mesh 30. This simplifies the device by foregoing any need for the controller 14 to transmit signals to effect transfer of CSF along the fluid conveyor, as the aerosol generator is effectively operable to pull CSF through the fluid conveyor. Nonetheless, in other examples, a more sophisticated fluid conveyor may be employed and the controller 14 may operate to transmit signals to both the fluid conveyor and the aerosol generator for separately controlling the transfer of CSF along the fluid conveyor and the conversion of CSF at the aerosol generator. In examples where the fluid conveyor and the aerosol generator are controlled separately, it is preferable the controller 14 be further adapted to synchronize a transport rate of CSF along the fluid conveyor and a conversion rate of CSF at the aerosol generator so as to ensure a steady state operation of the atomizer.

The controller 14 may further include a variable energy module 16 that is operable to vary the power output from the controller 14 to the one or more components controlled by the controller 14. In the example shown in FIG. 2, a variable energy module 16 may control the power output of the controller 14 to the transducer 20 between several different settings, including for example output voltages of 2.3 V DC, 3 V DC, and 5V DC at frequencies from approximately 110 kHz to approximately 120 kHz. When using a piezoelectric metal plate, the frequencies may range from approximately 40 kHz to approximately 120 kHz. The metal plate example is capable of generating aerosols at lower energy and frequency levels than the mesh example, though the droplets tend to shift to larger sizes at these lower levels. Droplets measuring approximately 10 microns or less are possible with the metal plate example at approximately 100 kHz. The variable energy input module 16 may be operable to change the power output in response to a user input and/or based on automated processing.

Non-limiting examples of constructions that may permit a user input to the variable energy module 16 may include: a knob on an external surface of the housing 10 that is adapted to protrude through the subject's skin, and which may be adjusted by manual rotation; a pressure switch on an external surface of the housing 10 that is adapted to reside under the subject's skin, and which may be adjusted by manual compressions applied to the subject's skin; and a wireless receiver contained within the housing 10, and which is operable to receive signals from an external wireless transmitter. In examples employing a wireless receiver, the external transmitter for communicating therewith may be contained in an external device 200/200', such as that shown in FIGS. 5 and 6A, which may be provided in the form of a communications device dedicated solely to communicating with the receiver of a specifically synced atomizer 1 (e.g., a dedicated radio transmitting device); or which may be provided in the form of a general purpose communications device that is adaptable to a multitude of different uses, including uses not related to the atomizer 1, though which is capable of syncing with the receiver of a specific atomizer 1 via a downloadable software application (e.g., an applications executing device, such as a smartphone, with a secure software application downloaded thereto).

A non-limiting examples construction in which the variable energy module 16 may operate to automatically change a power output of the controller 14 include the use of pre-programmed operational times, and the determination of CSF volume and volumetric changes within the reservoir 50. Examples employing pre-programmed operational times may be beneficial for subjects that experienced heightened production levels of CSF, as such a condition may require regular intervals of CSF removal at predetermined rates. In examples where atomizer operation is automated based on determinations of CSF volume, there may be employed one or more sensors. As shown in the example of FIG. 2, the atomizer 1 may include one or more fluid sensors 17a-17c positioned within the housing 10 and adapted for detecting one or more a fluid levels of CSF contained in the reservoir 50 and for outputting signals to the variable energy module 16 indicative of determined fluid levels. In such an example, the variable energy module 16 is operable to vary the power output of the controller 14 to correspond with changes in the determined volume of CSF within the reservoir 50, which may correspond with a low fluid level indication from sensor 17a, an intermediate fluid level indication from sensor 17b, and a high fluid level indication from sensor 17c. The variable energy module 16 could then adjust the transport and conversion rates of CSF to correspond with a determined volume of CSF in the reservoir 50, thereby enabling control of the atomizer 1 to correspond with variations of CSF production based on the subject's condition.

In some examples a multitude of fluid sensors 17a-17c may be arranged in varying positions and orientations the atomizer housing 10 to ensure adequate fluid level readings are obtained despite tilting of the atomizer 1 (e.g., as when a subject changes between standing and resting positions). For example, though the example in FIG. 2 shows three sensors 17a-17c positioned along a single vertical wall adjacent to the reservoir 50, in other constructions there may be provided a number of fluid sensors positioned at the base surface of the reservoir 50, while a number of fluid sensors are also positioned at a base surface of a first wall adjacent to the reservoir 50, and further while a number of fluid sensors are further positioned at a base surface of a second wall adjacent to the reservoir 50. Distribution of various sensors along a number of different walls of the housing 10 would facilitate accurate fluid level readings despite a tilting of the atomizer 1 in one direction or another—the accuracy of these readings could be yet further enhanced by adapting the controller 14 to perform a comparative analysis of signals that are received concurrently from multiple sensors.

The sensors 17a-17c, and the signals output to the variable energy module 16 therefrom, may also be used to synchronize a transport rate of CSF along the fluid conveyor and a conversion rate of CSF at the aerosol generator in examples where the fluid conveyor and the aerosol generator are controlled separately.

In some examples, the variable energy module 16 may be adapted to vary the power output of the controller 14 based on both user input and detected fluid volume, thereby enabling a user to adjust the rate of CSF conversion and misting as desired, while also setting one or more thresholds as safeguards to ensure adequate CSF conversion and misting to prevent accumulation of excess CSF in the reservoir 50. Both the user based and fluid level based controls may include a zero power setting such that the atomizer 1 may be powered down in response to either a user input or a determination that a CSF fluid level is below a predetermined threshold. Preferably, the controller 14 is configured to limit the circumstances under which a user may fully power down the atomizer, based on duration and/or detected fluid levels, so as to ensure adequate removal of CSF.

In examples where the power source 15 is provided as either a rechargeable power source or a power relay source, and in which the variable energy module 16 employs a wireless transceiver, the atomizer 1 may be adapted such that both the power source 15 and the variable energy module 16 communicate with a common external device 200/200', be it in the form of a special purpose dedicated communications device or a general purpose communications device that is synced by a software application.

The aerosol generator shown in the example of FIG. 2 is a piezoelectric mesh transducer, which includes a piezoelectric transducer 20 having a perforated mesh 30 at the center thereof. In such examples, the piezoelectric transducer 20 may include a silicon gasket that seals an end of the atomizer housing 10, with an embedded induction coil for receiving and converting electrical signals (either from an internal power source or an external device) into mechanical vibrations. The aerosol generator is not limited to the examples discussed above (e.g., the piezoelectric mesh transducer or the piezoelectric metal plate transducer), and may instead take any suitable form for converting CSF from a bulk liquid to an aerosol dispersion of ultrafine CSF droplets. Non-limiting examples of aerosol generators include: microelectromechanical (MEMS) devices; surface acoustic wave devices (including low sonic and ultrasonic transducers); surface vibration induced devices; electrostatic devices; and any other similar devices.

The fluid conveyor shown in the example of FIG. 2 is preferably a spring-loaded porous wick. The fluid conveyor is not limited to a porous wick, and may instead take any suitable form for conveying CSF from the reservoir to the aerosol generator. Non-limiting examples of fluid conveyors include: an absorbent silica gel, a cellulosic wick material, a bio-compatible foam material, and/or a fiberglass material adapted to convey fluid by capillary action; an electrostatic feed line adapted to convey fluid by electrostatic charge; and any other similar devices.

Figure 3A:
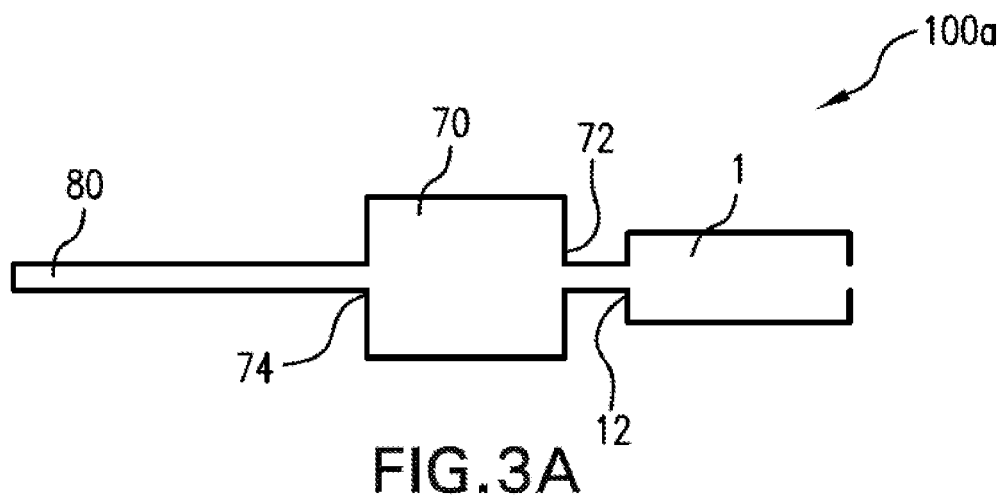
FIG. 3A shows a first example of a cranial implant comprising the atomizer of FIG. 2.
Figure 3B:
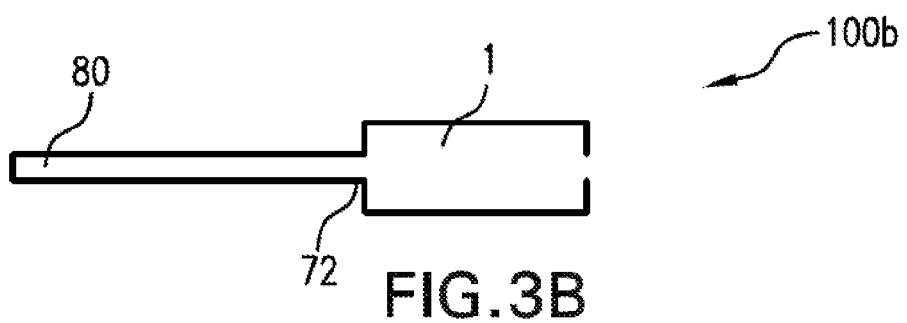
FIG. 3B shows a second example of a cranial implant comprising the atomizer of FIG. 2.

FIGS. 3A and 3B show two examples of a cranial implant 100a/100b incorporating the atomizer 1. In the cranial implant 100a, shown in FIG. 3A, the inlet 12 of the atomizer 1 communicates with an outlet 72 of a fluid chamber 70, the fluid chamber 70 having an inlet 74 that communicates with a ventricular catheter 80. In the cranial implant 100b, shown in FIG. 3B, the inlet 12 of the atomizer 1 communicates directly with the ventricular catheter 80.

Use of the cranial implant 100a may be preferable in instances when a medical provider may wish to have ready access to CSF that is in communication with the ventricle, in bulk liquid form. For example, a cranial implant 100a may be implanted such that the reservoir 70 is positioned just below the scalp or skin of the subject thereby enabling the medical provider to access CSF in the reservoir (e.g., via use a syringe to perforate a self-resealing surface of the reservoir 70, or via a valve built into the reservoir 70) so as to withdraw CSF in a bulk liquid form for testing purposes— e.g., testing for infection. When such access to CSF is not needed, then use of cranial implant 100b may be more preferable due to its smaller size.

Figure 4:
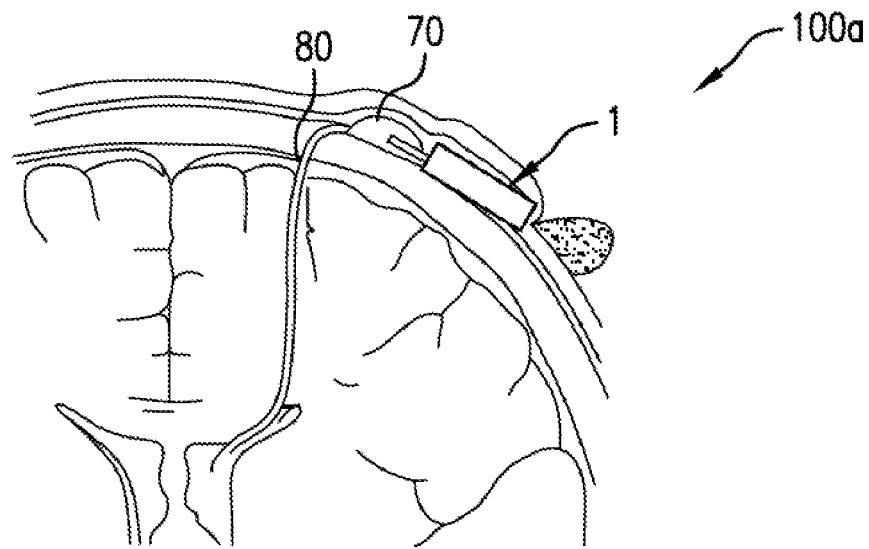
FIG. 4 shows an implanted atomizer of FIG. 2 in a subject.

In use the cranial implant 100a/100b is implanted with the catheter 80 inserted into a ventricle of a subject, and the atomizer 1 (as well as the fluid chamber 70, if provided) secured below the subject's scalp, as shown in FIG. 4. Specifically, a medical provider will create an incision into the scalp of the subject and drill a hole through the skull. A cranial implant 100a/100b is then implanted by inserting the free end of the ventricular catheter 80 through the hole in the scalp and into the subject's ventricles. A sealing agent may then be applied between the ventricular catheter 80 and the hole in the skull. The atomizer 1 (as well as the fluid chamber 70 if provided) is then secured to the exterior of the skull below the subject's scalp. The medical provider then seals the incision in the scalp, thereby enclosing the atomizer 1 (as well as the fluid chamber 70 if provided) under the subject's scalp.

In operation, excess CSF is drained from the subject's ventricles through the ventricular catheter 80 and fed to the reservoir 50 of the atomizer 1. Meanwhile, the controller 14 regularly outputs electrical signals that drive the fluid conveyor to convey fluid from the reservoir 50 to the aerosol generator and/or to drive the aerosol generator to convert CSF from a bulk liquid to an aerosol dispersion of ultrafine droplets. In examples such as that shown in FIG. 2, the controller 14 may output signals only to drive the piezoelectric transducer 20 to vibrate, which in turn will cause the vibration of the mesh 30 and a pumping action in the spring-loaded wick 40. When a sufficient volume of CSF is present in the reservoir 50 to submerge the bottom end 42 of the wick 40, vibration of the transducer 20 will effect a pumping action in the wick 40 that drives CSF up the wick 40 and through the perforations of the mesh 30, thereby producing a plume of ultrafine CSF droplets in a low-velocity aerosol. The CSF droplets are evaporated, and vapors are dissipated from the subcutaneous space by diffusion through the scalp and out of the body, or by diffusion into the capillary bed.

The atomizer implant 1 may measure approximately 3 cm×3 cm×1 cm, with the controller 14 being provided in the form of an electrical circuit plate measuring approximately 3 cm×3 cm×0.5 cm. The aerosol generator, when provided as a piezoelectric mesh transducer, may be in the form of a piezoelectric transducer 20 having a diameter of approximately 10 mm, with the perforated mesh 30 having a diameter of about 2 mm. The droplet size of an aerosol mist output from the atomizer 1 will depend on the nature of the aerosol generator and the physicochemical properties of the CSF. Preferably, the aerosol generator is adapted to output a CSF aerosol having ultrafine particles in the range of 0.5-10 microns, preferably 0.5-5 microns, and more preferably 0.5-2.5 microns. When the aerosol generator is provided as a piezoelectric mesh transducer, the droplet size of the CSF aerosol may be influenced by forming the perforations in the mesh 30 by an electroplating or laser perforation technique that forms microperforations suitable for achieving the ultrafine droplet sizes.

Figure 7:
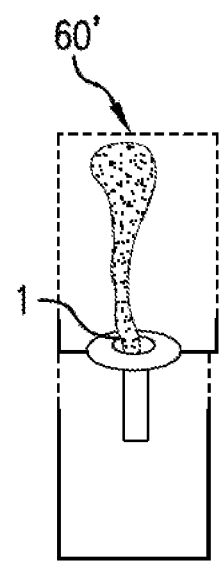
FIG. 7 is a schematic representation of a first prototype of an atomizer of FIG. 2.

Prototype subcutaneous biological atomizers were created to simulate generation, transport, diffusion and evaporation of a CSF aerosol plume through a human scalp. FIG. 7 shows a schematic of a first prototype atomizer 1' constructed with a piezoelectric mesh transducer and spring-loaded porous wick, as in the example of FIG. 2. Water was used to simulate CSF, and a mist column 60' constructed from a semipermeable membrane (DuPont™ Tyvek®) was used to simulate scalp tissue. The prototype was provided with a variable energy module adjustable between output voltages of 2.3 V DC, 3 V DC, 4.5V and 5V DC, and was set to generate mists having droplets measuring about 10 micron or less. A constant supply of water was maintained in the reservoir during testing to ensure the bottom end of the wick remained below the surface of the water, and that a steady mist rate was obtained.

FIGS. 8A and 8B are schematic representations as to the results observed with the first prototype. Specifically, as illustrated by FIG. 8A, at an ambient temperature of 20° C. it was found that the vaporized mist would deposit and soak into the semipermeable membrane 60'. On the other hand, as illustrated by FIG. 8B, at a temperature of 37° C. it was found that the vaporized mist readily dissipates by evaporation and diffusion through the semipermeable membrane 60'.

During testing it was observed that droplet size is influenced by the size of the perforations in the mesh and the vibration frequency, and that mass flow and aerosol plume height were influenced by energy input. Tests were conducted with an output frequency set at approximately 115 kHz, with input voltage (Watts supplied) being varied from 2.3 V DC to 5 V DC. As shown in the following Table 1, the resultant mist rate was observed to range from 0.35-0.9 ml/min, with plume heights observed from approximately 2 to 4 inches in height, depending on changes to input energy.

TABLE 1

| Voltage (DC) | Mist Rate (ml/min) | Mist Plume Height* (inch) |
| --- | --- | --- |
| 2.3 | 0.35 | 2 |
| 3 | 0.62 | 3 |
| 4.5 | 0.83 | 3.5 |
| 5 | 0.92 | 4 |

*Visible mist plume heights were approximated as observed at ambient temperature.

Without being bound by theory, testing of the first prototype is considered to confirm that an aerosolized CSF mist emitted in a subcutaneous cavity of a living subject having a body temperature of 37° C. will readily dissipate by evaporation of droplets within the cavity and diffusion of vapors through the subject's scalp or skin. Furthermore, it is considered that a mist rate of 0.35 ml/min may be desirable, though a preferred mist rate may vary depending on the rate of CSF production and the severity of CSF production/absorption imbalance experienced by a given subject. Mist plume height is considered indicative of the distance that CSF aerosol can be dispersed, and it is expected that plume height will decrease as temperature increases, with more immediate evaporation of CSF droplets expected at increased temperatures. Without being bound by theory, it is expected that temperatures approximating the human body temperature (e.g., 98.6° F./37° C.) are expected to result in plume heights below 6 inches, and as low as 1-2 cm.

FIG. 9 shows a schematic of a second prototype atomizer 1" constructed with a piezoelectric mesh transducer and spring-loaded porous wick, as in the example of FIG. 2. In this second prototype an atomizer 91 is mounted atop an airtight column 92 within an incubator 93, with the incubator 93 set to maintain a constant temperature of 37° C., so as to simulate a body temperature. Water was again used to simulate CSF, and the atomizer 91 was oriented to emit a vaporized mist 94 downwards into the airtight column 92. Within the airtight column 92, joined to a bottom surface of the atomizer 91, there was arranged a mist column 60"

constructed from a cylindrical mesh having a cadaver skin sample wrapped therearound. At a bottom end of the mist column 60", opposite the atomizer 91, there was positioned a collecting cap 95. In this second prototype the atomizer 91 was powered by a USB connection 96, though any suitable power source could have been used, including a battery.

Three separate tests were run with this second prototype. In each instance, the skin sample was weighed before being wrapped around the cylindrical mesh to construct the mist column 60", and the atomizer 91 was weighed along with the water. Misting was performed for a continuous five minutes, during which time there was observed a fogginess forking on the airtight column 92. This fogging is considered to have resulted from the vaporized mist diffusing through the skin sample and condensing on the inner surface of the airtight column 92, and is considered to further support the conclusion that an aerosolized CSF mist will diffuse through a subject's skin as sweat or perspiration. After conclusion of the five minute trial period, weighing was made of the skin sample, the atomizer with water, and the collecting cap 95 with condensed water. From these measurements, there was the calculated the mass of water misted by the atomizer 91, the mass of water absorbed in the skin sample, and the mass of water condensed in the collecting cap 95. There was then further calculated the mass of water that diffused through the skin, which was calculated based on the difference between mass misted and the sum of the mass collected in the collecting cap 95 and the mass absorbed in the skin sample.

Figure 10:
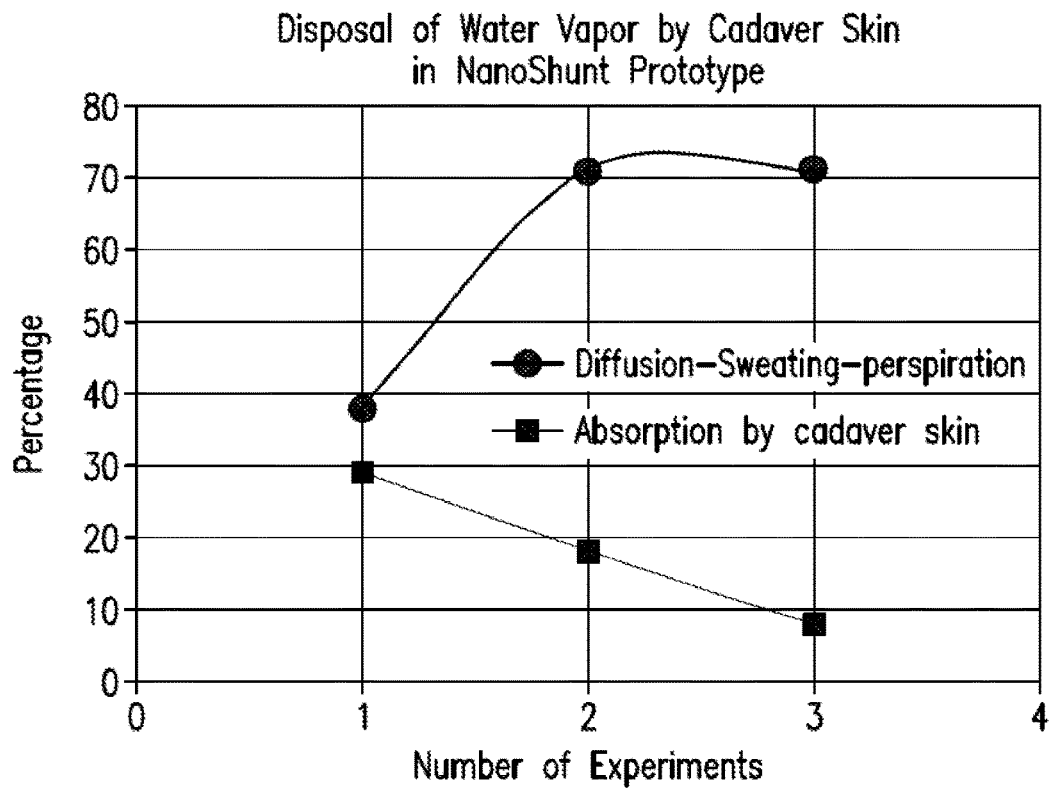
FIG. 10 is a graphical representation of comparative results from testing the second prototype, showing percentages of aerosolized fluid diffused and percentages of aerosolized fluid absorbed.

FIG. 10 is a graphical representation of the test results, showing the percentage of vapor that diffused through the skin sample and the percentage of vapor that was absorbed by the skin sample in each test of the second prototype. These results show that diffusion through the skin sample was the predominant mechanism of disposing of the water vapor, and suggest that diffusion will likewise be the predominant mechanism for disposing of CSF from a subject in the form of sweating/perspiration through the subject's skin. However, without being bound by theory, it is considered the absorption percentages observed in testing the second prototype might be relatively "reduced" due to the use of cadaver skin, as the use of dead tissues without blood circulation may be causing diffusion to play a more significant role, and greater absorption percentages might be realized with a real-life subject. It is also considered that the variations from test to test might be due to statistical variations in the experimental conditions and the sample skins.

Figure 11:
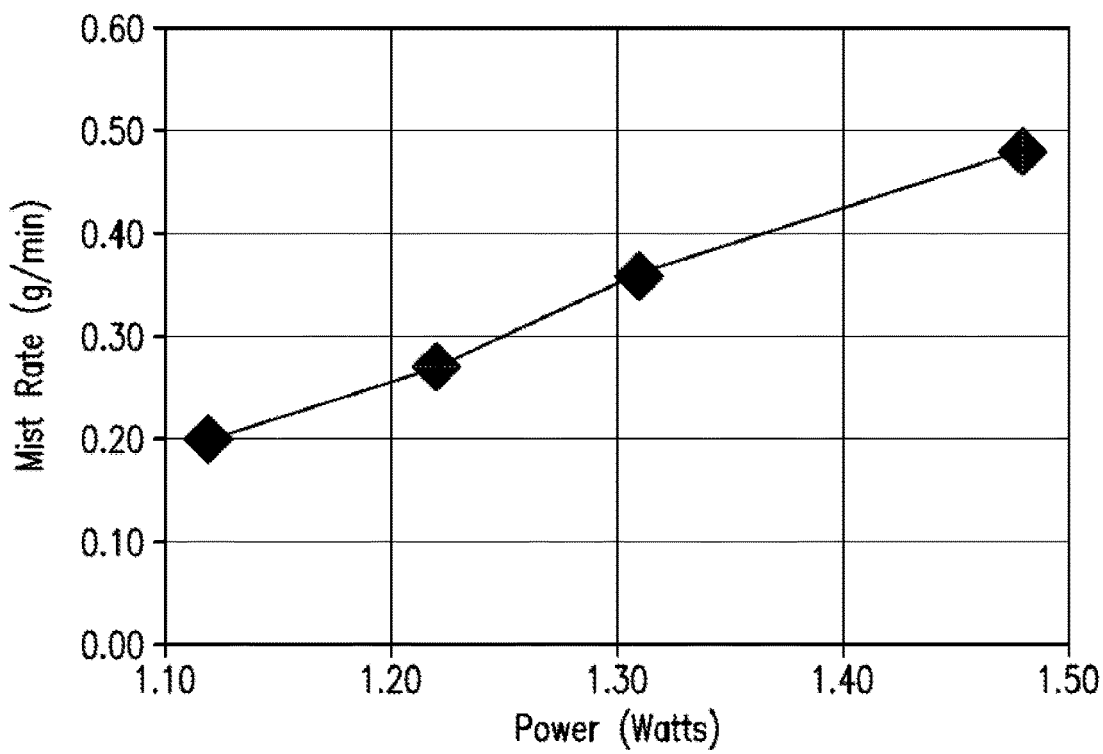
FIG. 11 is a graphical representation of a relationship between power input and mist rate.

FIG. 11 is a graphical representation showing a relationship between changes in mist rate with variations in input power (Watts) for a wireless cranial implant, as observed during testing of the second prototype. With recognition of such a relationship, it's possible to construct a cranial implant to have an adjustable mist rate by providing a user input for changing the mist rate, such as a power knob on an external transmitter. Alternatively, in a simplified form, a preferred mist rate may be determined for a particular subject's needs, and a cranial implant may be constructed operate under a preset power input for achieving the preferred mist rate for that subject's specific needs. In such a simplified construction, the controller may be adapted to switch the atomizer to a depowered state when it is determined that no fluid is being conveyed along the fluid conveyor (e.g., when a fluid sensor signals that the wick is in a dried state based on a charge conductivity of the wick).

Figure 12:
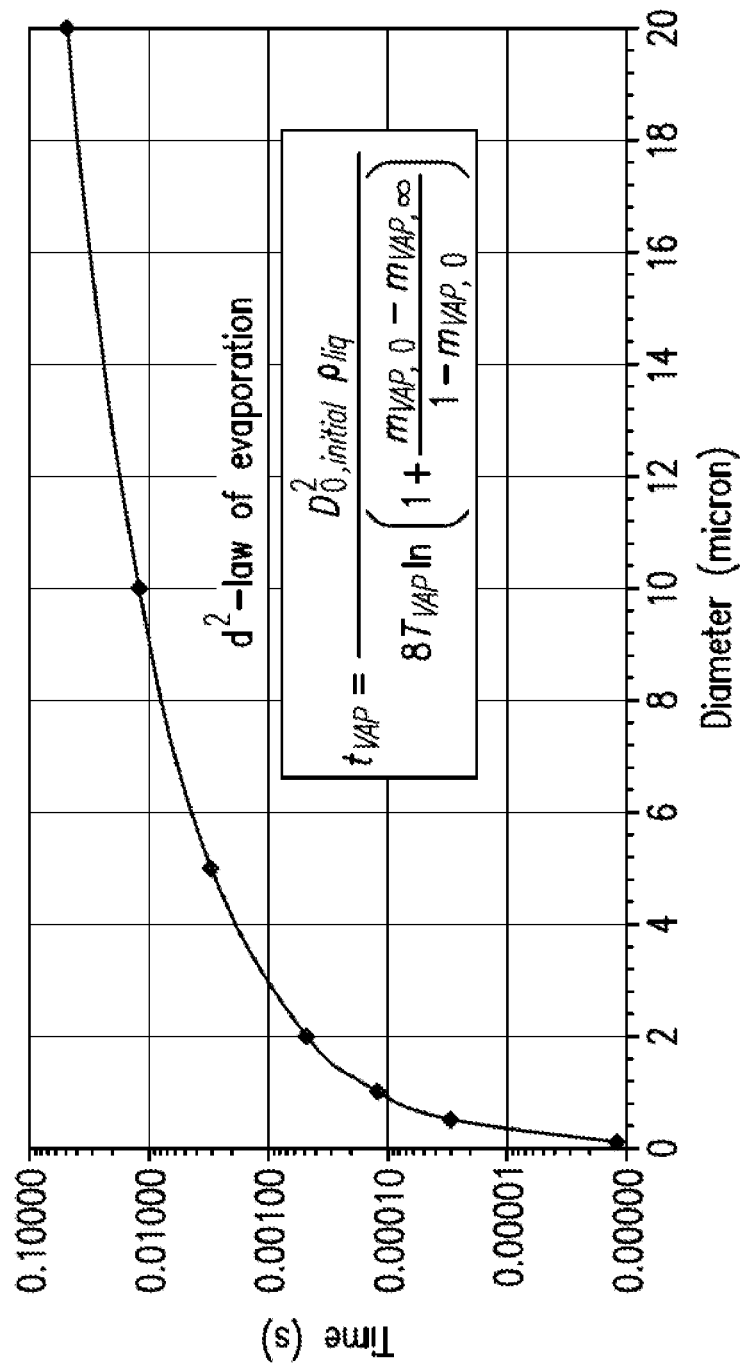
FIG. 12 is a graphical representation of a relationship between droplet evaporation and time.

FIG. 12 shows droplet evaporation, as calculated for a single droplet (approximation), using Professor Brian Spaulding's $d^2$-law of evaporation. As can be seen, a droplet measuring below 10 microns in diameter takes approximately 0.01 seconds to evaporate, and a droplet measuring below 5 microns in diameter takes approximately a millisecond to evaporate. At temperatures approximating the human body, it is expected that a majority of CSF aerosol droplets ejected by an implanted atomizer may evaporate instantaneously and completely as they are ejected, with remaining vapor being absorbed in capillary bed and transported into the bloodstream and/or diffused through the subject's skin as perspiration.

Although the present invention is described with reference to particular embodiments, it will be understood to those skilled in the art that the foregoing disclosure addresses exemplary embodiments only; that the scope of the invention is not limited to the disclosed embodiments; and that the scope of the invention may encompass additional embodiments embracing various changes and modifications relative to the examples disclosed herein without departing from the scope of the invention as defined in the appended claims and equivalents thereto.

Though the foregoing disclosure addresses examples of the method and device as applied to remove CSF in the treatment of hydrocephalus, methods and devices according to the present invention are not limited to those examples and may instead be used to remove other bodily fluids in effecting other treatments. For example, methods and devices according to the present invention may be used to remove excess peritoneal fluid from the abdominal cavity in the treatment of ascites; as well as the excess pleural fluid from the lungs in the treatment of such ailments as hydrothorax, hemothorax, urinothorax, chylothorax, or pyothorax.

The present invention is not limited to the exemplary embodiments illustrated herein, but is instead characterized by the appended claims.

What is claimed is:

1. A device for removing fluid in a subject's body, comprising:
    a housing having an inlet and an outlet, the inlet opening toward a reservoir for receiving bodily fluid;
    an aerosol generator positioned at the outlet of the housing, the aerosol generator configured for implantation in a subcutaneous space of the subject for converting a bulk liquid to an aerosol dispersion of ultrafine droplets; and
    a fluid conveyor extending from the aerosol generator and into the reservoir.

2. The device according to claim 1, wherein the aerosol generator comprises a piezoelectric transducer having a perforated mesh, the perforated mesh being positioned at the outlet of the housing.

3. The device according to claim 2, further comprising:
    a controller configured to output signals for controlling the piezoelectric transducer, wherein
    the controller is configured to output electrical signals to vibrate the piezoelectric transducer in a manner to effect a pumping action in the fluid conveyor that drives bodily fluid contained in the reservoir to travel along the fluid conveyor and through perforations in the perforated mesh to thereby produce a low-velocity aerosol containing droplets of the bodily fluid.

4. The device according to claim 3, wherein
    the perforations of the perforated mesh are dimensioned such that the aerosol output through the perforated mesh comprises droplets measuring 0.5 to 10 microns in diameter.

5. The device according to claim 3, wherein
the perforations of the perforated mesh are dimensioned such that the aerosol output through the perforated mesh comprises droplets measuring 0.5 to 5 microns in diameter.

6. The device according to claim 3, wherein
the perforations of the perforated mesh are dimensioned such that the aerosol output through the perforated mesh comprises droplets measuring 0.5 to 2.5 microns in diameter.

7. The device according to claim 3, wherein
the controller comprises a variable energy module configured to vary the power output to the piezoelectric transducer between two or more power settings.

8. The device according to claim 7, wherein
the variable energy module includes a zero-power setting for powering off the device.

9. The device according to claim 1, further comprising:
a fluid feed transport in fluid connection with the inlet of the housing for feeding bodily fluid to the reservoir of the housing.

10. The device according to claim 9, wherein
the fluid feed transport comprises a catheter.

11. The device according to claim 9, further comprising
a fluid chamber positioned in communication between the fluid feed transport and the inlet of the housing.

12. The device according to claim 1, wherein
the fluid conveyor comprises a porous wick joined to a side of the perforated mesh.

13. The device according to claim 12, wherein
the porous wick is a spring-loaded wick.

14. A method of removing fluid in a subject's body, comprising:
implanting the device according to claim 9 in a living subject with the fluid feed transport inserted into a target region in the subject's body.

15. The method according to claim 14, further comprising:
draining a bodily fluid from the target region to the reservoir in the housing of the device;
effecting conveyance of the bodily fluid along the fluid conveyor to convey the bodily fluid from the reservoir to the aerosol generator;
ejecting the bodily fluid through the aerosol generator in the form of an aerosol.

16. The method according to claim 15, wherein
the CSF aerosol is ejected to a space between the subject's skull and scalp.

17. The method according to claim 15, wherein
vapors of the aerosol are absorbed in the subject's capillary bed and/or diffused through subject's skin tissues.

18. The method according to claim 15, wherein
the aerosol is ejected with droplets measuring 0.5 to 10 microns in diameter.

19. The method according to claim 15, wherein
the aerosol is ejected with droplets measuring 0.5 to 5 microns in diameter.

20. The method according to claim 15, wherein
the aerosol is ejected with droplets measuring 0.5 to 2.5 microns in diameter.

21. The method according to claim 15, wherein
the target region is the subject's abdominal cavity, and the bodily fluid is peritoneal fluid.

22. The method according to claim 15, wherein
the target region is the subject's lungs, and the bodily fluid is pleural fluid.

23. The method according to claim 15, wherein
draining of the bodily fluid is performed as a treatment for an ailment chosen from: hydrothorax, hemothorax, urinothorax, chylothorax, and pyothorax.

24. The method according to claim 14, wherein
the target region is the subject's abdominal cavity.

25. The method according to claim 14, wherein
the target region is the subject's lungs.

26. A method of removing fluid in a subject's body, comprising:
draining fluid from a target region in the subject's body;
conveying the drained fluid along a fluid conveyor to an aerosol generator implanted in a subcutaneous space of the subject;
converting the fluid from a bulk liquid to an aerosol dispersion of ultrafine droplets; and ejecting the aerosol dispersion.

27. The method according to claim 26, wherein
the aerosol dispersion is ejected with droplets measuring 0.5 to 10 microns in diameter.

28. The method according to claim 26, wherein
the aerosol dispersion is ejected into a subcutaneous cavity and aerosol fluid droplets are then evaporated, and vapors are diffused through the skin and/or transported through the blood stream.

29. The method according to claim 26, wherein
the target region is the subject's abdominal cavity.

30. The method according to claim 26, wherein
the target region is the subject's lungs.

31. The method according to claim 26, wherein
the target region is the subject's abdominal cavity, and the fluid is peritoneal fluid.

32. The method according to claim 26, wherein
the target region is the subject's lungs, and the fluid is pleural fluid.

33. The method according to claim 26, wherein
draining of the fluid is performed as a treatment for an ailment chosen from: hydrothorax, hemothorax, urinothorax, chylothorax, and pyothorax.

* * * * *